United States Patent [19]
Luber et al.

[11] Patent Number: 5,891,020
[45] Date of Patent: Apr. 6, 1999

[54] MEDICAL THERAPEUTIC AND/OR DIAGNOSTIC APPLIANCE WITH A STERILIZABLE POSITION SENSING ATTACHMENT

[75] Inventors: Joachim Luber, Essingen-Forst; Ulrich Lemcke, Heidenheim; Christian Duschek, Heuchlingen; Arvids Mackevics, Aalen-Waldhausen; Hartmut Gärtner, Oberkochen, all of Germany

[73] Assignee: Carl-Zeiss-Stiftung, Germany

[21] Appl. No.: 731,368

[22] Filed: Oct. 11, 1996

[30] Foreign Application Priority Data

Oct. 12, 1995 [DE] Germany .................. 195 37 972.1

[51] Int. Cl.⁶ .................. A61B 5/103; A61B 6/00; A61N 1/00
[52] U.S. Cl. .................................................. 600/300
[58] Field of Search .................. 606/130; 600/300, 600/407, 417, 424, 427, 429

[56] References Cited

U.S. PATENT DOCUMENTS

| | | | |
|---|---|---|---|
| 5,213,113 | 5/1993 | Hlinsky et al. .................. | 607/129 X |
| 5,309,913 | 5/1994 | Kormos et al. .................. | 606/130 X |
| 5,383,454 | 1/1995 | Bucholz .................. | 606/130 X |
| 5,408,409 | 4/1995 | Glassman et al. .................. | 364/413.13 |
| 5,517,990 | 5/1996 | Kalfas et al. .................. | 606/130 X |

Primary Examiner—John P. Lacyk
Assistant Examiner—Samuel Gilbert

[57] ABSTRACT

A medical therapeutic and/or diagnostic appliance includes an arrangement that senses a position and attitude at any given time, and that includes a first sensing unit on the therapeutic and/or diagnostic appliance and a second sensing unit having a fixed location and attitude and arranged to be separated from the first sensing unit by a signal path. The first sensing unit is constructed, for reasons of sterilization and of position sensing, as an attachment that can be detached from the medical therapeutic and/or diagnostic appliance when in use. A coupling device is provided on the medical therapeutic and/or diagnostic appliance for installation of the attachment over a sterilizing sheath surrounding the therapeutic and/or diagnostic appliance.

10 Claims, 4 Drawing Sheets

MEDICAL THERAPEUTIC AND/OR DIAGNOSTIC APPLIANCE WITH A STERILIZABLE POSITION SENSING ATTACHMENT

BACKGROUND OF THE INVENTION

1. Field of the Invention

The present invention relates to a medical therapeutic and/or diagnostic appliance with an arrangement which senses its position and attitude at any given time and which comprises a first sensing unit on the therapeutic and/or diagnostic appliance, and a second sensing unit having a fixed location and attitude and arranged to be separated from the first sensing unit by a signal path.

2. Description of Prior Art

Such a therapeutic and/or diagnostic appliance is known, for example, from U.S. Pat. No. 5,408,409. This document shows as the first sensing unit a LED arrangement on the therapeutic appliance, embodied as a surgical cutting instrument, and spaced from it, a camera arrangement having a fixed location and attitude as the second sensing unit.

The prevention of infection is of great importance in medicine. Medical therapeutic and/or diagnostic appliances must therefore be sterilizable. Thus the therapeutic appliance known from U.S. Pat. No. 5,408,409 is surrounded, together with the first sensing unit which is fixedly attached to it, by a sterile sheath during an operation. An effective and reliable sterilization of the medical therapeutic and/or diagnostic appliances, which usually do not have a uniform, smooth surface, is thereby ensured, whereas it can only be achieved with difficulty by solely spraying with a sterilizing solution. On the other hand, however, sheathing the first sensing unit can lead to problems of reliability and accuracy of position and attitude sensing, with regard to achieving the most undistorted signal paths between the first and the second sensing unit, since a sterilizing sheath can interfere with the signal transmission between the first and the second sensing unit.

SUMMARY OF THE INVENTION

The invention therefore has as its object to make possible, in a therapeutic and/or diagnostic device of the relevant kind, both highly effective sterilization and also a reliable and precise sensing of its position and attitude.

According to a first aspect of the invention, this object is attained by an arrangement that detects the position and attitude of the therapeutic and/or diagnostic appliance. The arrangement includes a first sensing unit on the therapeutic and/or diagnostic appliance and a second sensing unit having a fixed location and attitude that is separated by a signal path from the first sensing unit. The first sensing unit is an attachment that can be attached and detached from the therapeutic and/or diagnostic appliance. The therapeutic and/or diagnostic appliance has a coupling device for installing the attachment (first sensing unit) over a sterilized sheath that surrounds the therapeutic and/or diagnostic appliance.

The first sensing unit, because of its configuration as an operationally detachable attachment, can be removed from the medical therapeutic and/or diagnostic appliance without complicated dismantling work. For preparation prior to its use, the therapeutic and/or diagnostic appliance is then effectively and quickly sterilized by pulling a sterilizing sheath over it in the usual manner. In parallel with this, the attachment, which is of small dimensions in comparison with the therapeutic and/or diagnostic appliance, and which can of course be configured as a compact unit, is sterilized, for example by spraying with a sterilizing solution. Since the separated attachment is much easier to sterilize than the therapeutic and/or diagnostic appliance, sheathing of the attachment can be dispensed with. Finally, the sterilized attachment is placed in its operational position, over the sterilizing sheath, by means of the coupling device formed on the therapeutic and/or diagnostic appliance.

By coupling of the sterilized first sensing unit to the therapeutic and/or diagnostic appliance, which has been sterilized by means of the sterilizing sheath, a high degree of sterility is ensured, and in addition sensing of position and attitude, unhindered by the sterilizing sheath, is made possible.

If the coupling device and the attachment have locating means which can be brought into mutual engagement, and by means of which a defined positional relationship can be produced between the attachment and the medical therapeutic and/or diagnostic appliance, a new measurement of this positional relationship after again removing, sterilizing and replacing the attachment can be dispensed with. Such locating means can be formed, for example, by locating pins formed on the attachment and, associated with these, locating pin recesses of the coupling device, and by a screw connection between the attachment and the coupling device.

The first sensing unit, constructed as an attachment, advantageously includes a transmitting device with at least three transmitting elements, e.g., LEDs, arranged spatially separated, and the coupling device includes control connections for these transmitting elements. Known position and attitude sensing devices can thus be used with sequentially controlled transmitting elements and with line cameras that perform sensing in a corresponding sequential manner.

When the attachment has a contour which corresponds to the surface contour of the therapeutic and/or diagnostic appliance, and more than three transmitting elements are arranged as far apart as possible, this results in an attachment which substantially fits closely to the therapeutic and/or diagnostic appliance and thereby does not hinder the manipulation of the therapeutic and/or diagnostic appliance. In addition, it is advantageous to avoid corners and angularities on the outside of the attachment, with regard to sterilizability and also with regard to position sensing. In this manner, there is a reduction of the sudden shadowing of the transmitting elements which is possible as a result of large movements of the therapeutic and/or diagnostic appliance, and which arises from edges moving into the respective signal paths between the individual transmitting elements and the second sensing unit. The provision of more than three, and preferably twelve, transmitting units also contributes to the enlargement of the region of movement of the therapeutic and/or diagnostic appliance, the suitable transmitting elements being selected on the basis of known distances of the transmitting elements from each other, or transmitting elements possibly leading to inexact position and attitude values can be segregated out.

It is particularly advantageous to use this invention in connection with an operation microscope that supplies focus parameter data to an evaluation unit associated with either the first or the second sensing unit. The first sensing unit, constructed as an attachment and provided for the sensing of the respective focus positions and the respective attitude of the optical axis of the operation microscope, can be attached to the operation microscope in a region which is relatively far from the patient and which is less problematic as regards sterilization. It is even possible to place the attachment on the other side of an axis of movement of an operation microscope (as seen by the patient) when by suitable sensors associated with the axis of movement a defined attitude relationship can always be produced between the attachment and the operation microscope. In this arrangement, the operation microscope is movably mounted on a stand, and the first sensing unit is not arranged on the operation microscope proper, but on a portion of the stand adjacent the operation microscope. The attachment, or the first sensing unit, can also remain in the sensing region of the second sensing unit by means of such measures, even when there are considerable attitude and position changes of the operation microscope.

Corresponding to a second aspect of the present invention, the object of the invention is also attained by a therapeutic and/or diagnostic appliance of the pertinent kind in which the first sensing unit has a convex outer surface and a setting edge for a clamping element. A sterilizing sheath which surrounds the therapeutic and/or diagnostic appliance, and which tends, for example, to crease and to cover an object multiple times, can thereby be fitted tightly over the first sensing unit by means of a clamping element, and thus in a manner which hinders as little as possible the signal path to the second sensing unit.

BRIEF DESCRIPTION OF THE DRAWINGS

The following description, which refers to the accompanying drawings, serves to facilitate understanding of the invention, in which.

DETAILED DESCRIPTION OF PREFERRED EMBODIMENTS

Figure 1:
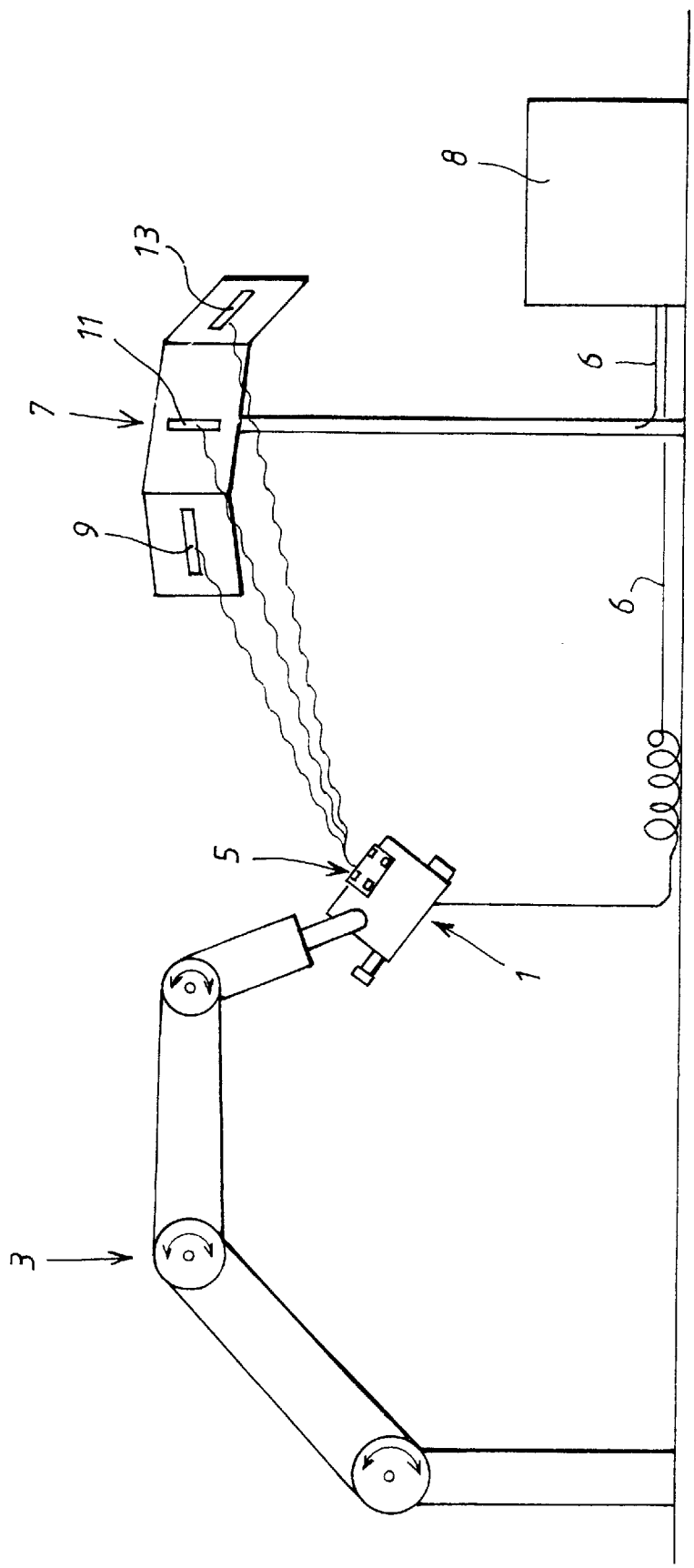
FIG. 1 shows a schematic illustration of an operation microscope as a first embodiment according to the first aspect of the invention.

The medical therapeutic and/or diagnostic appliance 1 which is schematically represented in FIG. 1 is an operation microscope which is displaceable and pivotable by means of a jointed stand 3. In order to sense the attitude of the operation microscope 1 at any given time, a position and attitude sensing arrangement is provided, with a first sensing unit 5 on the operation microscope 1 and a second sensing unit 7, which is fixed in location and attitude. The first sensing unit 5 and the second sensing unit 7 are connected by leads 6, which are shown schematically, to a position and attitude evaluation unit 8. Since the position and attitude sensing on which this kind of invention is based depends on a direct signal transmission, e.g., by light or ultrasonics, between the first sensing unit 5 and the second sensing unit 7, the second sensing unit 7, constituted in this mode of embodiment by an arrangement of three line cameras 9, 11, 13, is to be as far as possible arranged so that the signal path from the first sensing unit 5, which is constituted as the transmitting device, is free from obstacles.

Figure 2:
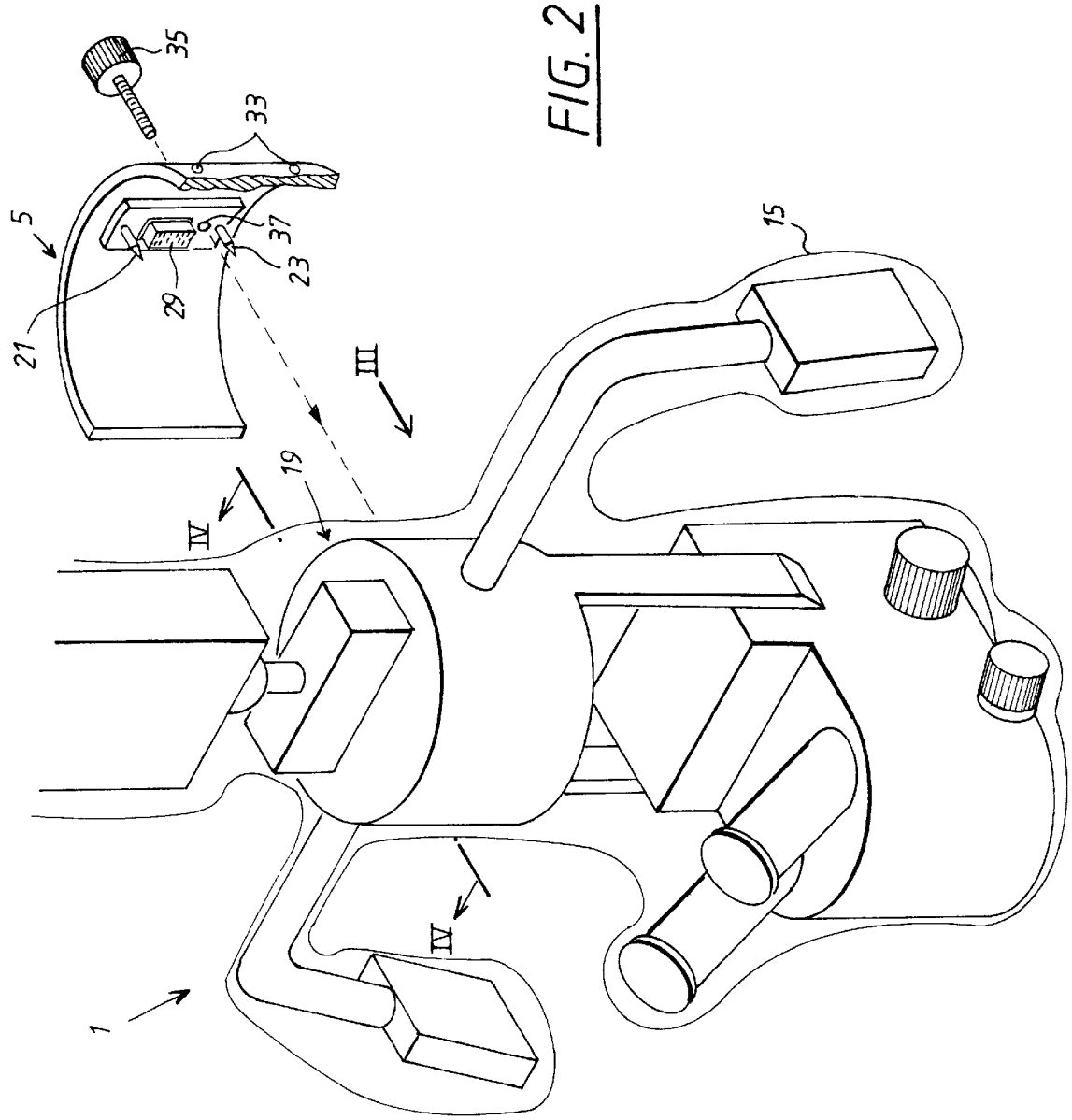
FIG. 2 is a perspective illustration of the operation microscope of FIG. 1, with a first sensing unit which has been detached from it.

FIG. 2 shows the first sensing unit, which according to the invention is constructed as an attachment 5 that is detachable when in use, and the operation microscope 1, in their state separated from each other. The operation microscope 1, which is already prepared for the operation, is surrounded by a (schematically indicated) sterilizing sheath 15.

Figure 3:
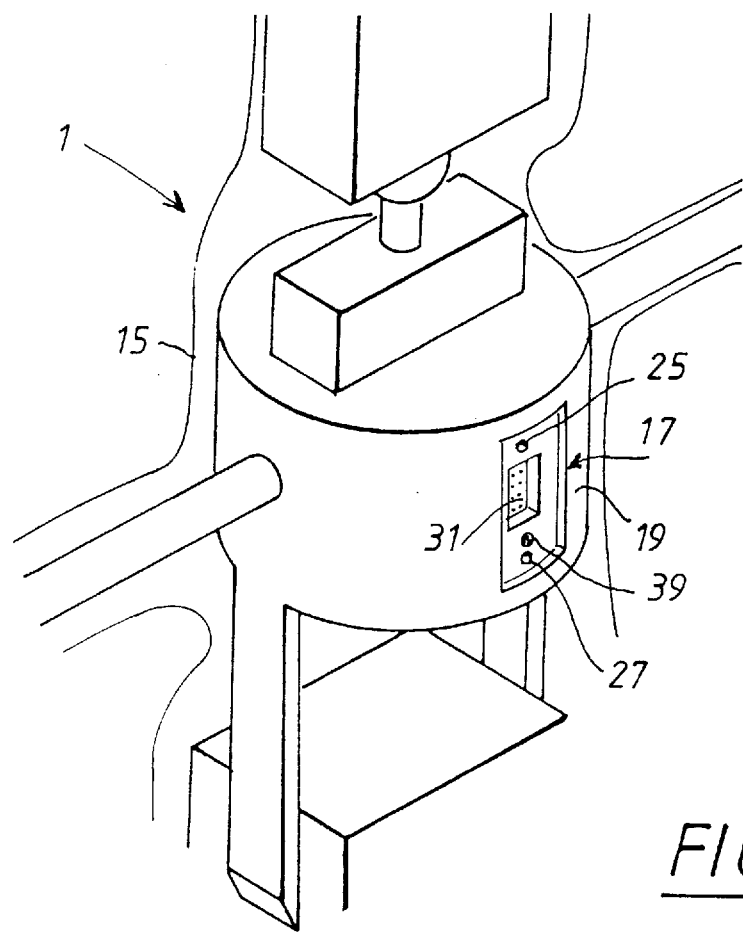
FIG. 3 shows a view of the operation microscope of FIG. 2 seen from the direction of the arrow of FIG. 2.

Associated with the attachment 5, a coupling device 17 on the operation microscope 1 can be seen in FIG. 3, which shows, in a perspective view seen in the direction of the arrow III of FIG. 2, the region 19 of the operation microscope 1 onto which the attachment 5 is to be fitted.

In FIG. 2, locating pins 21 and 23 can be seen, which are on the inner side of the attachment 5, face towards the operation microscope 1, pierce through the sterilizing sheath 15 when the attachment 5 is seated on the operation microscope 1, and engage in locating pin recesses 25 and 27 (FIG. 3) of the coupling device 17. Furthermore, a plug contact device 29 is provided on the inner side of the attachment 5, and produces, by engagement in a plug contact receptacle device 31 (FIG. 3) of the coupling device 17, a control lead for the transmitting elements 33, which are in the form of LED's. The transmitting elements 33 are arranged on the outside of the attachment 5, facing towards the second sensing unit 7. Furthermore, a knurled screw 35 contributes to producing a defined attitude relationship between the attachment 5 and the operation microscope 1, and can be screwed into a threaded hole 39 (FIG. 3) of the coupling device 17.

Figure 4:
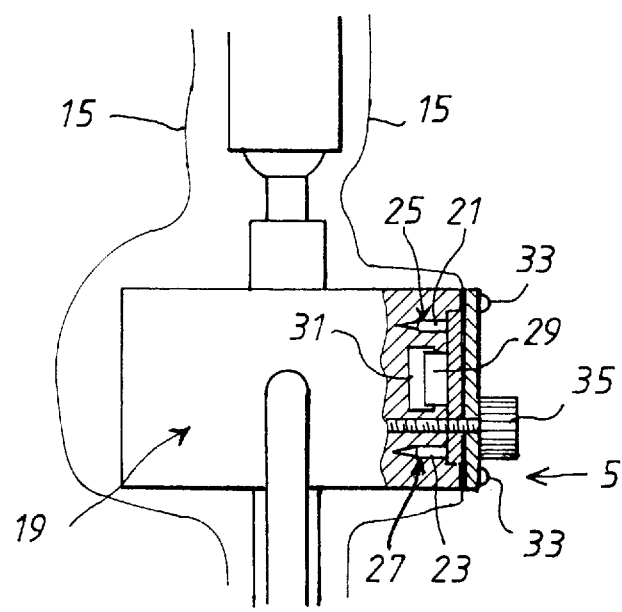
FIG. 4 shows a schematic cross section along the line IV—IV of FIG. 2.

The section 19 of the operation microscope with the attachment 5 fitted over the sterilizing sheath 15 is shown schematically in cross section in FIG. 4.

Figure 5:
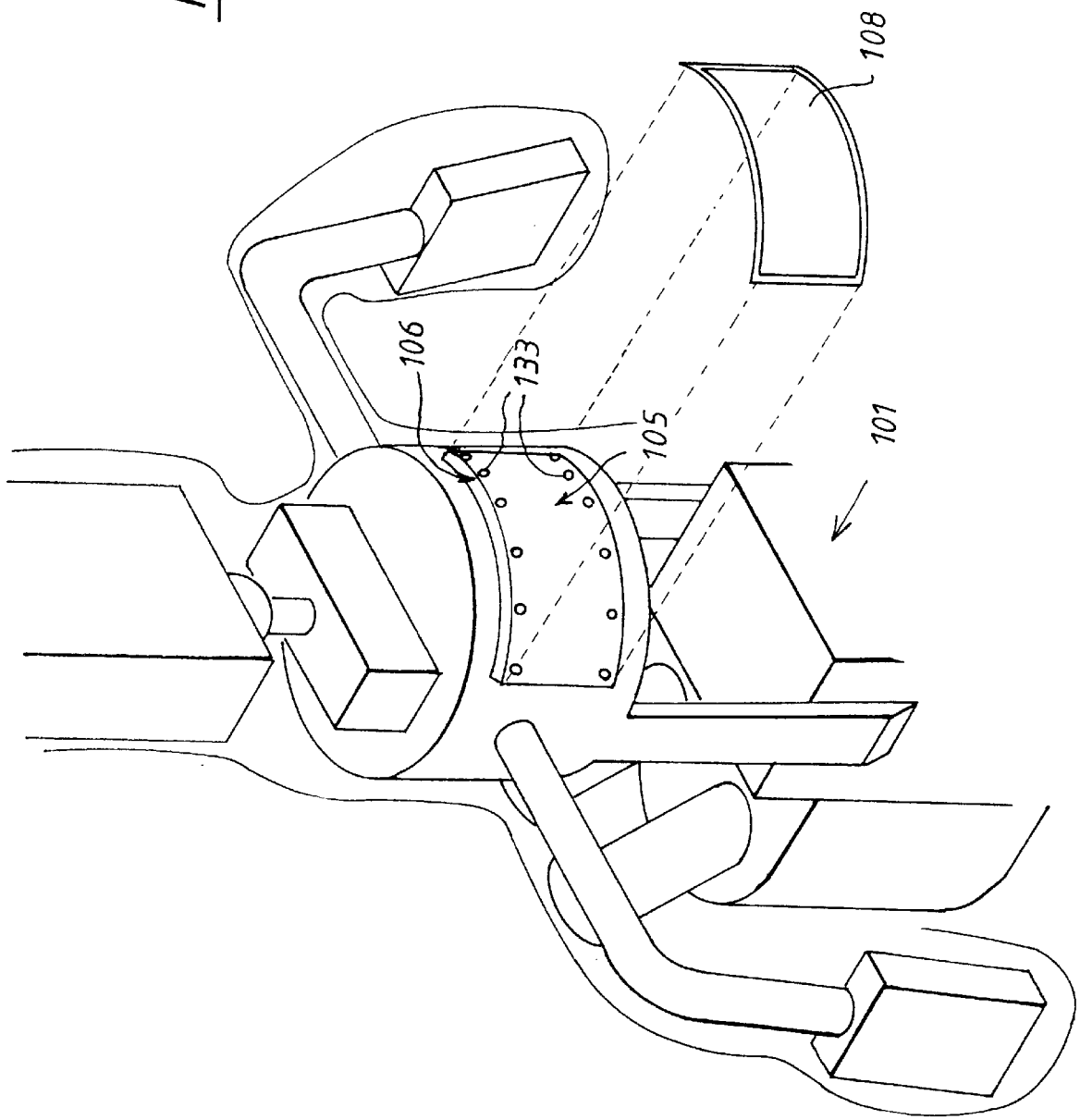
FIG. 5 shows a perspective illustration of a second embodiment of the invention, disclosing the second aspect of the invention.

An embodiment according to the second aspect of the invention is shown in FIG. 5. Here the components have the corresponding reference numbers, increased by 100, of the corresponding components in FIGS. 1–4.

Corresponding to the second aspect of the invention, the first sensing unit 105 has a setting edge 106 for a clamping element, formed by a step between the first sensing unit 105 and the region of the operation microscope 101 surrounding it. However, the setting edge for a clamping element can also be formed by a surrounding undercut at the edge of the first sensing unit 105. Associated with the surrounding step 106 is a clamping element 108, which can be sterilized without problems, for example, a clamping frame 108 formed according to the contour of the first sensing unit 105, or else a rubber-elastic O-ring. The clamping frame 108 can be arranged on the first sensing unit 105 by tightly fitting over a sterilizing sheath. By this means, a sterilizing sheath, which is slipped over the operation microscope 101 including the first sensing unit 105, can be pulled tight, free from folds and overlaps, in the region of the sensing unit 105, and can be kept permanently and reliably tight by fixing the clamping element 108 on the clamping element setting edge 106. In this manner, obstruction of the signal path between the transmitting elements 133 and the second sensing unit is kept as small as possible.

We claim:

1. An arrangement (5, 7) which detects the position and the attitude of a medical appliance at any given time, comprising
    a medical appliance,
    a sterilizing sheath that surrounds the medical appliance,
    a first sensing unit (5) that is detachable from the medical appliance, and
    a second sensing unit (7) of fixed location and attitude, separated by a signal path from the first sensing unit (5),
    in which the first sensing unit (5) comprises an attachment that can be attached and detached from a coupling device (17) on the medical appliance for installation of the attachment over the sterilizing sheath (15).

2. The arrangement (5, 7) according to claim 1, wherein the coupling device (17) and the attachment (5) have setting devices (21, 23, 25, 27, 35, 37, 39) designed to be brought into mutual engagement for producing a defined attitude relationship between the attachment (5) and the medical appliance.

3. The arrangement (5, 7) according to claim 2, wherein the setting devices include locating pins (21, 23) on a side of the attachment (5) associated with the coupling device (17), locating pin recesses (25, 27) for receiving the locating pins (21, 23) on the coupling device (17), and a screw connection (35, 37, 39) between the attachment (5) and the coupling device (17).

4. The arrangement (5, 7) according to claim 1, wherein the attachment (5) includes a transmitting device with at least three transmitting elements (33), arranged in a spatial distribution, and the coupling device (17) includes control connections (31) for the transmitting elements.

5. The arrangement (5, 7) according to claim 4, wherein the attachment (5) has a convex contour that corresponds to the surface contour of the medical appliance, and more than three transmitting elements (33) are arranged on the convex outer side of the attachment and directed towards the second sensing unit.

6. The arrangement (5, 7) according to claim 1, wherein the medical appliance is an operation microscope (1) which provides focusing parameter data to an evaluation unit (8) associated with one of the first and the second sensing units (5, 7).

7. The position and attitude sensing units (5, 7) for a movable medical appliance (1) according to claim 1.

8. The coupling device (17) according to claim 1.

9. The arrangement according to claim 1, wherein the first sensing unit is coupled to a movement axis of the medical appliance, and a sensor unit associated with the medical appliance ensures a defined position and attitude relationship between the medical appliance and the first sensing unit.

10. An arrangement which senses the position and attitude of a medical appliance (1) at any given time, comprising:

a medical appliance (1), a first sensing unit (5) on the medical appliance (1), a second sensing unit (7) of fixed location and attitude, separated by a signal path from the first sensing unit (5), wherein the first sensing unit (105) has a convex outer surface which is directed towards the second sensing unit and has a clamping element setting edge (106) for a clamping element (108).

* * * * *